United States Patent [19]

Niwa

[11] Patent Number: 5,119,822
[45] Date of Patent: Jun. 9, 1992

[54] PULSE WAVE DETECTING APPARATUS

[75] Inventor: Minoru Niwa, Nagoya, Japan

[73] Assignee: Colin Electronics Co., Ltd., Aichi, Japan

[21] Appl. No.: 508,609

[22] Filed: Apr. 13, 1990

[30] Foreign Application Priority Data

Oct. 19, 1988 [JP] Japan .................................. 63-263562

[51] Int. Cl.$^5$ ............................................... A61B 5/02
[52] U.S. Cl. .................... 128/672; 128/687; 128/690
[58] Field of Search .................... 128/677, 687-690, 128/695, 696, 701, 713-715, 679, 680, 681, 672

[56] References Cited

U.S. PATENT DOCUMENTS

| 4,461,266 | 7/1984 | Hood, Jr. et al. | 128/681 |
| 4,799,491 | 1/1989 | Eckerle. | |
| 4,836,213 | 6/1989 | Wenzel et al. | 128/672 |
| 4,947,855 | 8/1990 | Yokoe et al. | 128/672 |
| 4,951,679 | 8/1990 | Harada | 128/672 |

FOREIGN PATENT DOCUMENTS

8803387  5/1988  World Int. Prop. O. .

Primary Examiner—Stephen C. Pellegrino
Assistant Examiner—Steven J. Shumaker
Attorney, Agent, or Firm—Oliff & Berridge

[57] ABSTRACT

A pulse wave detecting apparatus including a pulse wave sensor; a pressing device for pressing the sensor against an arterial vessel of a subject, while varying the pressing force; a first device for determining an amplitude of each of pulses of pulse wave which are detected by the sensor while the pressing force is varied; a second device for determining, based on the determined pulse amplitudes, a first range of the pressing force within which the pulse amplitudes are generally constant, the first range including a point at which a rate of change of the pulse amplitudes with respect to the pressing force is zero; a third device for determining a minimum value of each of the pulses detected by the sensor; a fourth device for determining, based on the determined pulse minimum magnitude, a second range of the pressing force within which the pulse minimum magnitudes are generally constant, the second range including a point at which a rate of change of the pulse minimum magnitudes with respect to the pressing force is minimum; a fifth device for determining an optimum range of the pressing force based on the first and second ranges, and determining an optimum value of the pressing force such that the optimum value falls within the optimum range; and a sixth device for adjusting the pressing device to the optimum pressing force, and obtaining a pulse wave of the subject through the sensor pressed with the optimum pressing force.

12 Claims, 3 Drawing Sheets

PULSE WAVE DETECTING APPARATUS

BACKGROUND OF THE INVENTION

1. Field of the Art

The present invention relates to an apparatus for detecting a pulse wave produced from an arterial vessel of a subject.

2. Related Art Statement

There is known a pulse wave detecting apparatus including (1) a pulse wave sensor having a press surface on which one or more pressure sensing elements are provided, the pulse wave sensor being pressed against an arterial vessel of a subject via a body surface above the arterial vessel so that the one or more pressure sensing elements detect a pulse wave produced from the arterial vessel of the subject, (2) pressing means for pressing the pulse wave sensor against the arterial vessel via the body surface, while varying the pressing force over a predetermined force range, and (3) means for determining an optimum, pulse wave sensor pressing force based on the pulse wave (pulses of the pulse wave) which is detected by the one or more pressure sensing elements while the pressing force is varied, and (4) means for obtaining a pulse wave of the subject through the pulse wave sensor pressed with the thus determined optimum pressing force. The conventional apparatus determines as the optimum pulse wave sensor pressing force a pressing force at which the pulse wave sensor (one or more pressure sensing elements) detects a pulse of the pulse wave whose amplitude is maximum, namely, the greatest of the amplitudes of the pulses detected by the pulse wave sensor in the process of varying the pressing force.

However, generally the thus determined optimum pressing force does not fall to around the middle value of a pressing force range which covers pressing force values at which a pulse wave having a sufficiently great amplitude is detected. Accordingly, in the event that the pulse wave sensor pressing force is changed from the optimum pressing force to a greater or smaller value due to physical motion of the subject or other causes, the conventional apparatus may fail to detect a pulse wave having a sufficiently great amplitude.

SUMMARY OF THE INVENTION

It is therefore an object of the present invention to provide a pulse wave detecting apparatus capable of detecting a pulse wave having a sufficiently great amplitude irrespective of change in the pulse wave sensor pressing force.

The above object has been achieved by the present invention, which provides a pulse wave detecting apparatus for detecting a pulse wave produced from an arterial vessel of a subject, comprising (a) a pulse wave sensor having a press surface on which at least one pressure sensing element is provided, the pulse wave sensor being pressed against an arterial vessel of a subject via a body surface above the arterial vessel so that the at least one pressure sensing element detects a pulse wave produced from the arterial vessel of the subject, (b) pressing means for pressing the pulse wave sensor against the arterial vessel via the body surface, while varying the pressing force over a predetermined force range, (c) first means for determining an amplitude of each of pulses of the pulse wave which are detected by the at least one pressure sensing element while the pressing force of the pressing means is varied, (d) second means for determining, based on the pulse amplitudes determined by the first means, a first force range of the pressing force within which the pulse amplitudes are generally constant, the first force range including a point at which a rate of change of the pulse amplitudes with respect to the pressing force is zero, (e) third means for determining a minimum magnitude of the each pulse of the pulse wave detected by the at least one pressure sensing element, (f) fourth means for determining, based on the pulse minimum magnitudes determined by the third means, a second force range of the pressing force within which the pulse minimum magnitudes are generally constant, the second force range including a point at which a rate of change of the pulse minimum magnitudes with respect to the pressing force is minimum, (g) fifth means for determining an optimum force range of the pressing force based on the first and second force ranges, and determining an optimum value of the pressing force such that the optimum value falls within the optimum force range, and (h) sixth means for adjusting the pressing means to the optimum value of the pressing force, and obtaining a pulse wave of the subject through the pulse wave sensor pressed against the arterial vessel with the optimum pressing force.

In the pulse wave detecting apparatus constructed as described above, the optimum force range of the pulse wave sensor pressing force is determined based on the first force range within which the pulse amplitudes are generally constant and which covers a pressing force at which the pulse wave sensor has detected a pulse having a maximum amplitude, and the second force range within which the pulse minimum magnitudes is generally constant. So long as the pulse wave sensor is pressed with a pressing force falling within the optimum force range, the pulse wave sensor detects a pulse wave whose amplitude is sufficiently great and generally constant. Accordingly, even in the event that the pulse wave sensor pressing force is changed due to physical motion of the subject or the like during the pulse wave detection, the present apparatus continues to detect a pulse wave having a sufficiently great amplitude.

According to a feature of the present invention, in the event that neither the first force range nor the second force range is zero, the fifth means determines as the optimum force range an overlap portion of the first and second force ranges. In the event that a value $\Delta Pc$ obtained by subtracting a lower limit Pcmin of the overlap potion from an upper limit thereof is smaller than a first predetermined value S, the fifth means may determine the optimum pressing force Pa according to the following expression: $Pa = Pcmin + \Delta Pc/2$, and, in the event that the value $\Delta Pc$ is not smaller than the first predetermined value S, the fifth means may determine the optimum pressing force Pa according to the following expression: $Pa = Pcmin + S/2$.

According to another feature of the present invention, in the event that the first force range is not zero and the second force range is zero, the fifth means determines the first force range as the optimum force range. In the event that a value $\Delta Pp$ obtained by subtracting a lower limit Ppmin of the first force range from an upper limit thereof is smaller than a second predetermined value T, the fifth means may determine the optimum pressing force Pa according to the following expression: $Pa = Ppmin + \Delta Pp/2$, and, in the event that the value $\Delta Pp$ is not smaller than the second predetermined value T, the fifth means determines the optimum pressing force according to the following expression: $Pa = Ppmin + T/2$.

According to yet another feature of the present invention, the pulse wave detecting apparatus further comprises means for, in the event that the first force range is zero, informing an operator that a position of the pulse wave sensor on the body surface with respect to the arterial vessel is inappropriate, and causing the apparatus to be deactivated.

According to a further feature of the present invention, the pressing means comprises (1) a housing, (2) a diaphragm fluid-tightly secured to inner surfaces of the housing, the diaphragm cooperating with the housing to define a fluid-tight pressure chamber, the pulse wave sensor being secured to an outer surface of the diaphragm so that the pulse wave sensor is movable together with the diaphragm relative to the housing, (3) supply means for supplying the pressure chamber with a pressurized fluid so as to press the pulse wave sensor against the arterial vessel via the body surface, and (4) pressure regulating means for regulating the pressurized fluid supplied to the pressure chamber and thereby adjusting a fluid pressure in the pressure chamber, the pressing force of the pressing means with which the pulse wave sensor is pressed against the arterial vessel being varied as the fluid pressure is varied by the pressure regulating means.

In a preferred embodiment of the present invention, the pulse wave sensor comprises a semiconductor chip of monocrystalline silicon, and a plurality of pressure sensing diodes provided in a row on one surface of the semiconductor chip, the one surface of the semiconductor chip serving as the press surface of the pulse wave sensor, each of the plurality of pressure sensing diodes detecting a pulse wave produced from the arterial vessel.

In another embodiment of the present invention in which the at least one pressure sensing element comprise a plurality of pressure sensing elements, (a) the first means determines an amplitude of each of pulses of the pulse wave which are detected by each of the plurality of pressure sensing elements while the pressing force of the pressing means is varied, (b) the second means selects as an optimum pressure sensing element one of the plurality of pressure sensing elements which element has detected a pulse whose amplitude is the greatest of the amplitudes of the pulses detected by the plurality of pressure sensing elements, and determines the first force range based on the amplitudes of the pulses detected by the optimum pressure sensing element, (c) the third means determines an minimum magnitude of each of the pulses detected by the optimum pressure sensing element, and (d) the fourth means determines the second force range based on the pulse minimum magnitudes determined by the third means. In the case where the plurality of pressure sensing elements comprise at least three pressure sensing elements provided in a row on the press surface of the pulse wave sensor, the apparatus may further comprises means for, in the event that the second means selects as the optimum pressure sensing element one of two pressure sensing elements respectively positioned at opposite ends of the row, discarding the pressure sensing element selected by the second means, and re-selecting as the optimum pressure sensing element another pressure sensing element which has detected a pulse whose amplitude is the greatest of the amplitudes of the pulses detected by the at least three pressure sensing elements except the discarded pressure sensing element.

In yet another embodiment of the present invention, the apparatus further comprises means for displaying and recording the pulse wave detected through the pulse wave sensor pressed with the optimum pressing force.

In a further embodiment of the present invention, the apparatus further comprises means for determining a blood pressure of the subject based on the pulse wave detected through the pulse wave sensor pressed with the optimum pressing force.

BRIEF DESCRIPTION OF THE DRAWINGS

The above and optional objects, features and advantages of the present invention will be better understood by reading the following detailed description of the presently preferred embodiment of the invention when considered in connection with the accompanying drawings in which.

DETAILED DESCRIPTION OF THE PREFERRED EMBODIMENT

Figure 1:
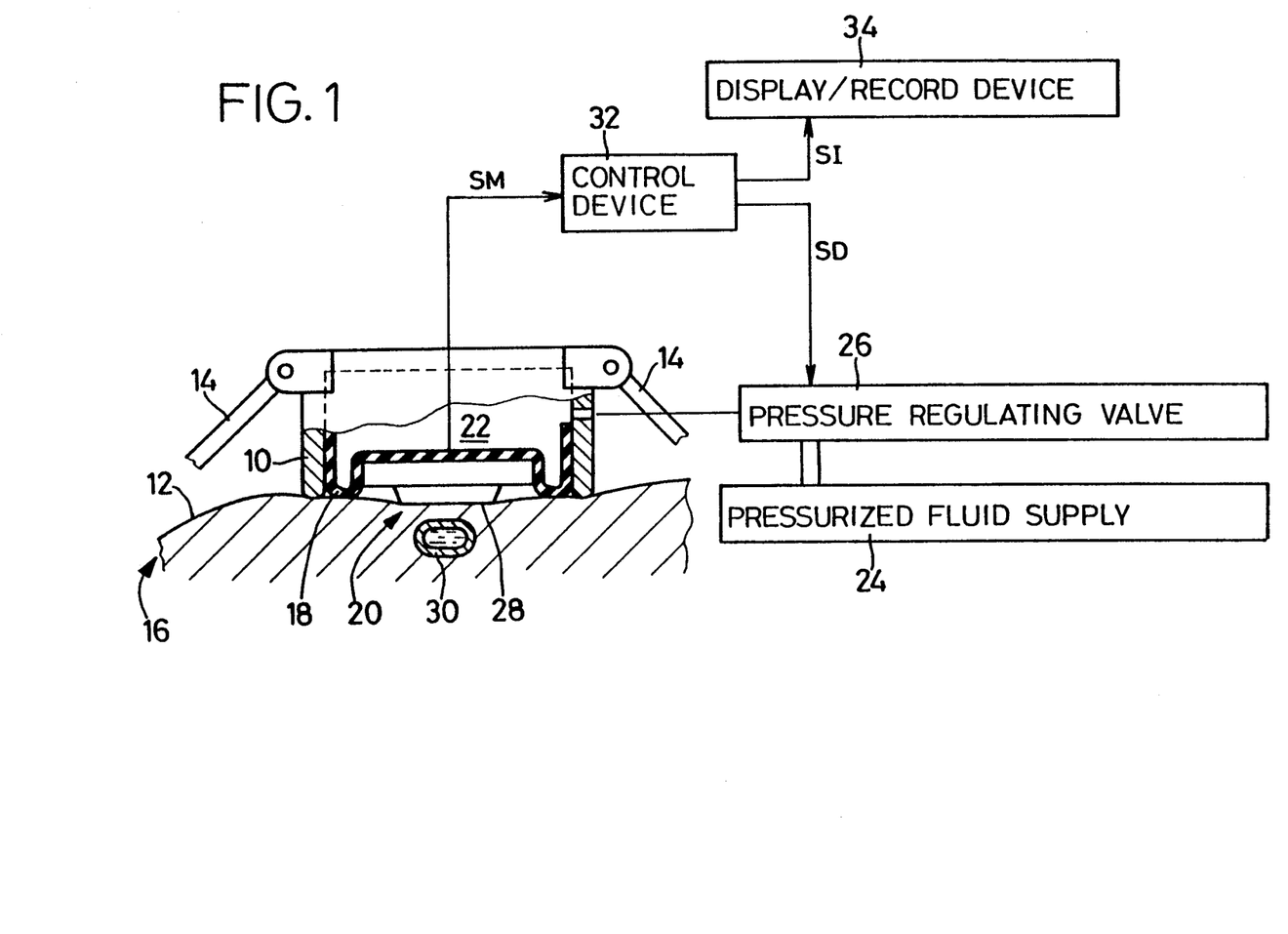
FIG. 1 is a view illustrating the circuit of the pulse wave detecting apparatus of the present invention.

Referring first to FIG. 1 there is illustrated a pulse wave detecting apparatus embodying the present invention. In the figure reference numeral 10 designates a cylindrical housing having a bottom end and an open end. The housing 10 is detachably set on a body surface 12 of a wrist 16 of a subject with the help of a band 14, with the open end of the housing 10 being opposed to the body surface 12. A diaphragm 18 is fluid-tightly secured to inner surfaces of the housing 10, and cooperates with the housing 10 to define a fluid-tight pressure chamber 22. A pulse wave sensor 20 for detecting pulse wave is secured to an outer surface of the diaphragm 18. A pressurized fluid supply 24 supplies the pressure chamber 22 with a pressurized fluid such as pressurized air. A pressure regulating valve 26 regulates the pressurized air supplied to the pressure chamber 22 and thereby adjusts an air pressure P in the pressure chamber 22. As the air pressure P in the pressure chamber 22 is increased or decreased, the diaphragm 18 is inflated or deflated and the pulse wave sensor 20 is displaced together with the diaphragm 18 relative to the housing 10, so that the pulse wave sensor 20 is advanced out of the open end of the housing 10 and is pressed against the body surface 12 with a pressing force corresponding to an air pressure P in the pressure chamber 22.

Figure 2:
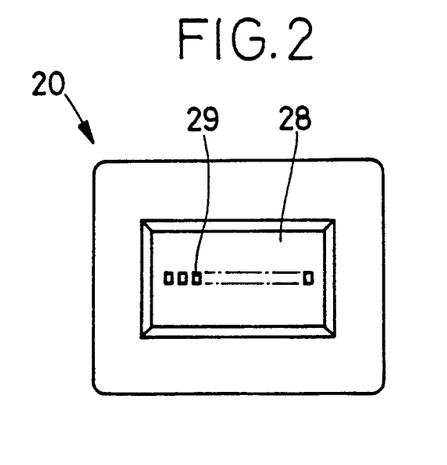
FIG. 2 is a view of a pulse wave sensor of the apparatus of FIG. 1, as viewed from the side of a body surface of a subject.

As shown in FIG. 2 the pulse wave sensor 20 is constituted by a semiconductor chip formed of, for example, monocrystalline silicon, and a multiplicity of pressure sensing elements 29, for example fifteen pressure sensing diodes, provided in a row on one surface 28 of the semiconductor chip. Thus, the chip surface 28 serves as a press surface at which the pulse wave sensor 20 is pressed against the body surface 12. With the housing 10 being attached to the wrist 16, the row of the pressure sensing elements 29 extends in a direction generally perpendicular to a radial artery 30 extending adjacent to a radius bone of the wrist 16. In other words, the pulse wave sensor 20 is pressed against the radial artery 30 via the body surface 12 such that the row of the pressure sensing elements 29 generally perpendicularly intersects the radial artery 30. In this situation, each pressure sensing element 29 detects an oscillatory pressure wave, namely, pressure pulse wave (hereinafter, abbreviated to "pulse wave") transmitted thereto from the radial artery 30 via the body surface 12. The pulse wave consists of successive pulses, and the pulses are produced from the radial artery 30 in synchronization with heartbeat of the subject. Each of the pressure sensing elements 29 converts the detected pulse wave to an electric signal (hereinafter, referred to as "pulse wave signal") SM, and supplies the pulse wave signal SM to a control device 32.

The control device 32 includes a microcomputer, and supplies a drive signal SD to the pressure regulating valve 26 according to pre-stored programs so as to adjust the air pressure P in the pressure chamber 22 in the housing 10. The control device 32 stores pulse wave signals SM supplied from the pressure sensing elements 29, while commanding the pressure regulating valve 26 to increase the air pressure P at a constant, low rate. Based on the stored pulse wave signals SM the control device 32 selects an optimum pressure sensing element 29A out of the multiplicity of pressure sensing elements 29 and determines an optimum pressing force Pa with which the pulse wave sensor 20 (optimum pressure sensing element 29A) is to be pressed against the radial artery 30. With the pulse wave sensor 20 being pressed with the optimum pressing force Pa, the control device 32 is supplied with a pulse wave signal SM from the optimum pressure sensing element 29A, and supplies a display/record signal SI representative of the pulse wave, to a display/record device 34. Thus, the display/record device 34 displays and records the pulse wave detected by the optimum pressure sensing element 29A pressed with the optimum pressing force Pa.

There will be described the operation of the pulse wave detecting apparatus constructed as described above, by reference to the flow chart of FIG. 3.

Figure 3:
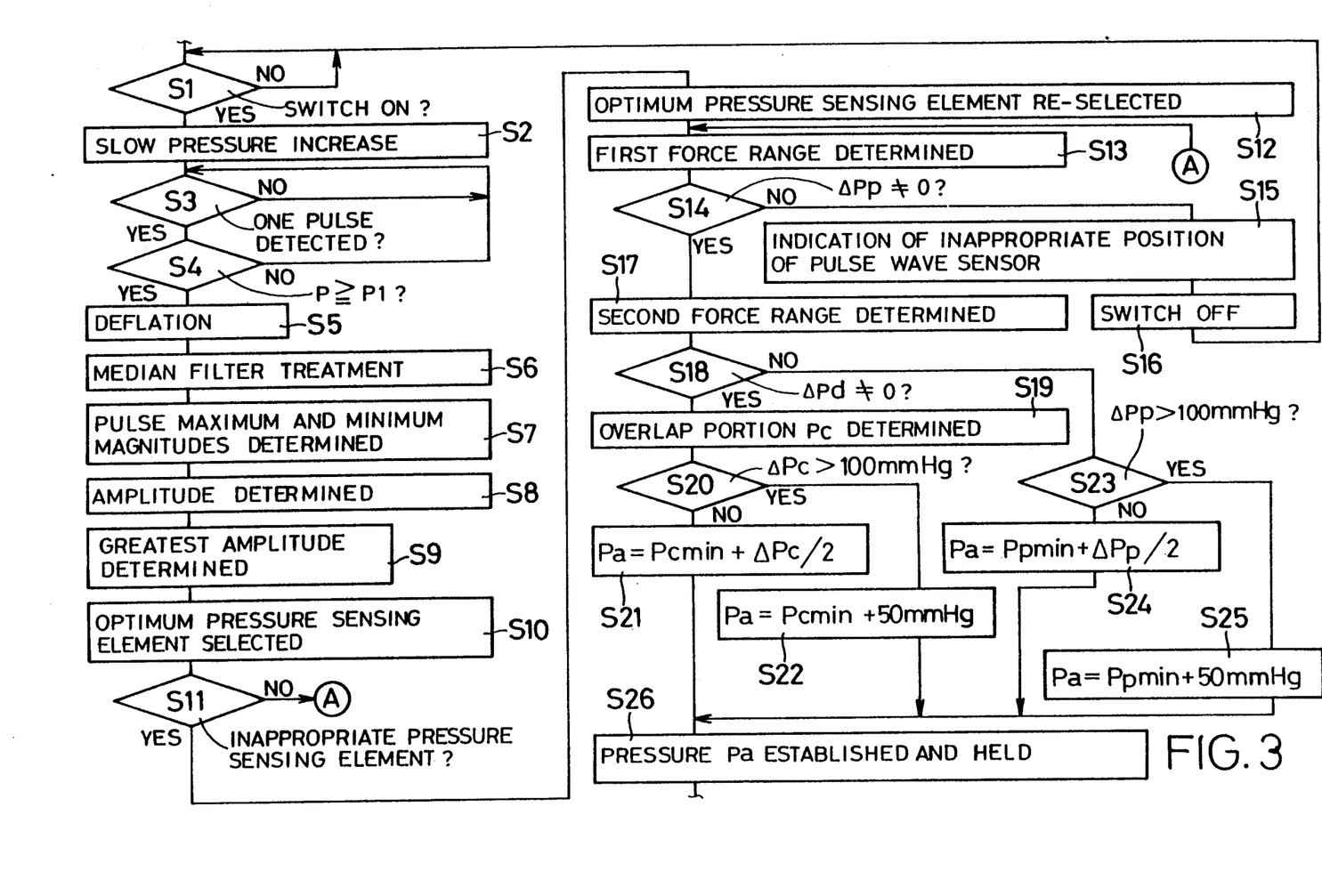
FIG. 3 is a flow chart according to which the apparatus of FIG. 1 is operated.

Upon application of electric power to the present apparatus, the control of the microcomputer of the control device 32 begins with Step S1 in which it is judged whether or not an ON/OFF switch (not shown) has been operated by an operator, namely, placed in an ON position thereof. If the judgement in Step S1 is negative (NO), Step S1 is repeated awaiting an operation of the ON/OFF switch. On the other hand, if it is judged in Step S1 that the ON/OFF switch is placed in the ON position thereof, namely, if the judgement in Step S1 is affirmative (YES), the control proceeds to Step S2 in which the air pressure P in the pressure chamber 22 is increased at a constant low rate, namely, slowly increased. Step S2 is followed by Step S3 in which it is judged based on the pulse wave signals SM whether or not in this slow pressure increase process the pressure sensing elements 29 have detected a length of pulse wave corresponding to one time heartbeat of the subject, namely, one pulse. If the judgement in Step S3 is negative, Step S3 is repeated. Meanwhile, if the judgement in Step S3 is affirmative, namely, if the pressure sensing elements 29 have detected one pulse of the pulse wave, the control device 32 stores pulse wave signals SM corresponding to the pulse, together with the corresponding values of the air pressure P in the pressure chamber 22. Subsequently, the control proceeds to Step S4 in which it is judged whether or not the air pressure P has exceeded a predetermined pressure level P1, for example about 200 mmHg. If the judgement in Step S4 is negative, namely, if the air pressure P has not reached the level P1, Steps S3 and S4 are repeated so that the control device 32 stores the pulse wave signals SM corresponding to a multiplicity of pulses of the pulse wave. On the other hand, if the judgement in Step S4 is affirmative, the control proceeds to Step S5 in which the pressurized air in the pressure chamber 22 is removed to decrease the air pressure P to atmospheric pressure.

Step S5 is followed by Step S6 in which the control device 32 applies a well-known median filter, a statistical treatment, to the stored pulse wave signals SM with respect to, for example, every five successive pulses of the signals SM, so as to remove artifact noise therefrom, namely, smooth the signals SM. Step S6 is followed by Step S7 in which the control device 32 determines a maximum and a minimum magnitude of each of the pulses with respect to each of the filtered signals SM. Step S7 is followed by Step S8 in which the control device 32 determines an amplitude of each of the pulses based on the maximum and minimum magnitudes thereof determined in Step S7. Thus, in the present embodiment Step S7 and a portion of the control device 32 for carrying out Step S7 cooperate with each other to serve as means for determining a minimum magnitude of each of pulses of the pulse wave detected by the pulse wave sensor, while Step S8 and a portion of the control device 32 for carrying out Step S8 cooperate with each other to serve as means for determining an amplitude of each of pulses of the pulse wave detected by the pulse wave sensor.

Subsequently, the control proceeds to Step S9 in which the control device 32 determines a maximum amplitude with respect to each of the pulse wave signals SM, namely, each of the pressure sensing elements 29. The maximum amplitude is the greatest amplitude of all the amplitudes of the pulses detected by the each pressure sensing element 29. Step S9 is followed by Step S10 in which the control device 32 selects as an optimum pressure sensing element 29A one of the pressure sensing elements 29 whose maximum amplitude is the greatest of all the maximum amplitudes of the pressure sensing elements 29. Step S10 is followed by Step S11 in which it is judged whether or not either one of the two pressure sensing elements positioned at opposite ends of the row of the pressure sensing elements 29 has been selected as the optimum pressure sensing element 29A. If the judgement in Step S10 is negative, the control proceeds to Step S13. On the other hand, if the judgement is affirmative, the control proceeds to Step S12 in which the control device 32 discards the pressure sensing element selected as the optimum pressure sensing element 29A in Step S11 and re-select as the optimum pressure sensing element 29A another pressure sensing element whose maximum amplitude is the greatest second to the maximum amplitude of the discarded pressure sensing element. Step S12 is followed by Step S13.

In Step S13 the control device 32 utilizes the amplitudes of the pulses detected by the optimum pressure sensing element 29A in the previously described slow pressure increase process, and the corresponding values of the air pressure P in the pressure chamber 22 (corresponding to pressing forces with which the pulse wave sensor 20 is pressed against the radial artery 30), for determining a first force range in which the pulse amplitudes are generally constant. The first force range includes a point at which the rate of change of the pulse amplitudes with respect to the air pressure values P (corresponding to the pulse wave sensor pressing forces) is zero. This point corresponds to a pressing force at which the optimum pulse wave sensor 29A has detected the pulse having the maximum amplitude. The first force range is determined such that the difference between the maximum pulse amplitude and each of the other pulse amplitudes is smaller than a considerably small value corresponding to, for example 7 mmHg in terms of pressure. The first force range is shown at Pp in the graph of FIG. 4, in which the pulse amplitudes are represented by a curved line A for easy understanding. In the present embodiment Step S13 and a portion of the control device 32 for carrying out Step S13 cooperate with each other to serve as means for determining the first force range of the pulse wave sensor pressing force.

Figure 4:
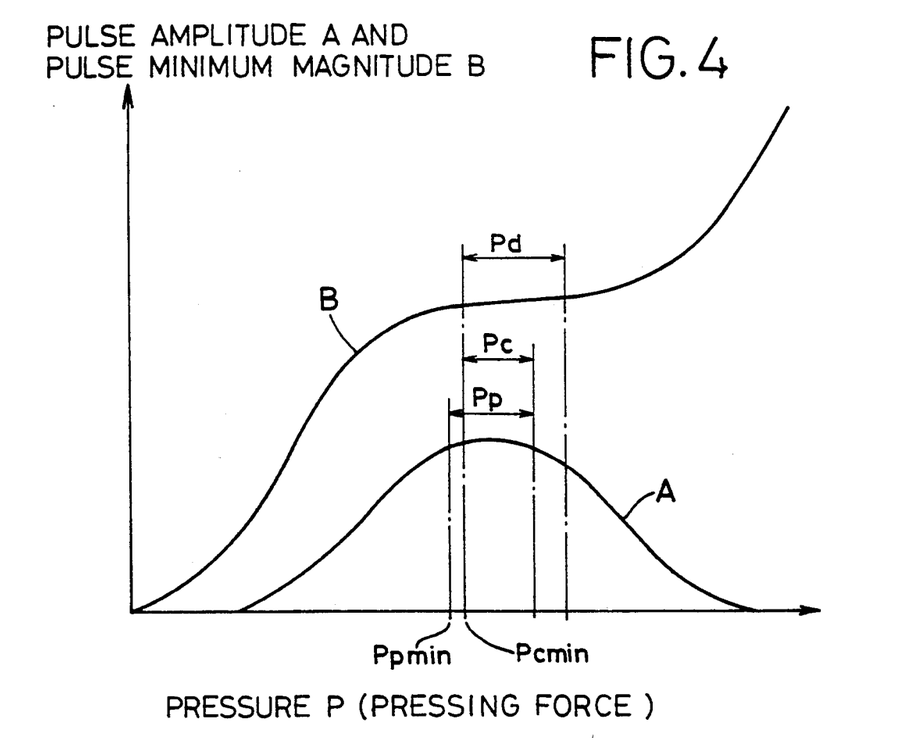
FIG. 4 is a graph showing a curve representative of change of the pulse amplitudes with respect to the pulse wave sensor pressing forces, and a curve representative of change of the pulse minimum magnitudes with respect to the pulse wave sensor pressing forces.

Step S13 is followed by Step S14 in which it is judged whether a value ΔPp obtained by subtracting a lower limit Ppmin of the first force range Pp from an upper limit of the same, is not zero, that is, whether or not the first force range Pp has any length, or exist, along the axis of abscissa of the graph of FIG. 4. If the judgement in Step S14 is negative (NO), namely, if the first force range Pp is zero, that means that a position of the pulse wave sensor 20 on the body surface 12 with respect to the radial artery 30 is inappropriate, and the control goes to Step S15 in which the control device 32 commands the display/record device 34 to display a predetermined indication informing the operator of this situation. Step S15 is followed by Step S16 in which the control device 32 causes the ON/OFF switch to be placed in the OFF position, thereby deactivating the present apparatus, and then the control returns to Step S1. However, since the ON/OFF switch has just been placed in the OFF position, the judgement in Step S1 is negative and Step S1 is repeated awaiting for another operation of the ON/OFF switch.

On the other hand, if the judgement in Step S14 is affirmative (YES), that is, if the first force range Pp is not zero, the control goes to Step S17 in which the control device 32 utilizes the minimum magnitudes of the pulses detected by the optimum pressure sensing element 29A, and the corresponding air pressure values P, for determining a second force range in which the pulse minimum magnitudes are generally constant. The second force range includes a point at which the rate of change of the pulse minimum magnitudes with respect to the air pressure values P is minimum. The second force range is determined such that the difference between a selected one of the pulse minimum values and each of the other pulse minimum values is smaller than a considerably small value corresponding to, for example 7 mmHg in terms of pressure. The second force range is shown at Pd in the graph of FIG. 4, in which the pulse minimum magnitudes are represented by a curved line B for easy understanding. In the present embodiment Step S17 and a portion of the control device 32 for carrying out Step S17 cooperate with each other to serve as means for determining the second force range of the pulse wave sensor pressing force.

Curves A and B of FIG. 4 correspond to upper and lower curves shown in FIG. 6 of U.S. Pat. No. 4,836,213 to Wenzel et al. The reason why each curve A, B changes with respect to increase in pressing force, and the manner how the curves can have corresponding pressing force values for what are considered one point in one curve (A) as a maximum pulse amplitude and another point in another curve (B) as a minimum rate of change (i.e., slope), is described at Column 6, Line 65 through Column 7, Line 27 and Column 7, Lines 55-60 of the above U.S. Patent. In this connection, it is noted that, in the upper graph of FIG. 6 of the above-noted patent, pulse amplitudes can be said to be accurately equal to respective blood pressure differences between systolic and diastolic blood pressures, with respect to only data points plotted within a hold-down pressure (or pressing force) range in which the pulse amplitudes are generally constant, and that, in the lower graph of FIG. 6 of the above-noted patent, diastolic pressures can be said to be accurate with respect to only data points plotted within a hold-down pressure range in which the diastolic pressures are generally constant.

Step S17 is followed by Step S18 in which it is judged whether a value ΔPd obtained by subtracting a lower limit Pdmin of the second force range Pd from an upper limit of the same, is not zero, that is, whether or not the second force range Pd has any length, or exists, along the axis of abscissa of the graph of FIG. 4. If the judgement in Step S17 is affirmative (YES), that is, if the second force range Pd is not zero, the control advances to Step S19 in which the control device 32 determines as an optimum force range an overlap portion Pc of the first and second force ranges pp and Pd. Step S19 is followed by Step S20 in which it is judged whether or not a value ΔPc obtained by subtracting a lower limit Pcmin of the optimum force range Pc from an upper limit of the same is greater than, for example, 100 mmHg. If the judgement in Step S20 is negative, that is, if the value ΔPc is not greater than 100 mmHg, the control goes to Step S21 in which the control device 32 determines an optimum air force Pa corresponding to an optimum, pulse wave sensor pressing force according to the following expression: Pa=Pcmin+ΔPc/2. On the other hand, if the judgement in Step S20 is affirmative, that is, if the value ΔPc is greater than 100 mmHg, the control goes to Step S22 in which the control device 32 determines the optimum air force Pa according to the following expression: Pa=Pcmin+50 mmHg.

Meanwhile, if the judgement in Step S18 is negative, that is, if the second force range Pd is zero, the control device 32 determines the first force range Pp as the optimum force range, and the control goes to Step S23 in which it is judged whether or not a value ΔPp obtained by subtracting a lower limit Ppmin of the first force range Pp (optimum force range) from an upper limit of the same, is greater than, for example, 100 mmHg. If the judgement in Step S23 is negative, that is, if the value ΔPc is not greater than 100 mmHg, the control goes to Step S24 in which the control device 32 determines the optimum air force Pa according to the following expression: Pa=Ppmin+ΔPp/2. On the other hand, if the judgement in Step S23 is affirmative, that is, if the value ΔPp is greater than 100 mmHg, the control goes to Step S25 in which the control device 32 determines the optimum air force Pa according to the following expression: Pa=Ppmin+50 mmHg.

In the present embodiment Steps S18 through S25 and a portion of the control device 32 for carrying out Steps S18-S25 cooperate with each other to serve as means for determining an optimum force range of the pulse wave sensor pressing force based on the first and second force ranges, and determining an optimum value of the pressing force such that the optimum value falls within the optimum force range.

After the determination of the optimum air pressure Pa (optimum value of the pulse wave sensor pressing force) in Step S21, S22, S24 or S25, the control goes to Step S26 in which the control device 32 controls the pressure regulating valve 26 to increase the air pressure P in the pressure chamber 22 to the optimum air pressure Pa and hold the air pressure Pa. As a result, the pulse wave sensor 20 is pressed against the radial artery 30 with an optimum pressing force corresponding to the optimum air pressure Pa. With the pulse wave sensor 20 being pressed with the optimum pressing force (Pa), the present apparatus obtains a pulse wave of the subject through the optimum pressure sensing element 29A, and commands the display/record device 34 to display and record the thus obtained pulse wave. The control device 32 may be adapted to determine a blood pressure of the subject based on the thus obtained pulse wave and command the display/record device 34 to display and record the thus determined blood pressure.

As emerges from the foregoing description, the present pulse wave detecting apparatus utilizes a pulse wave (pulses thereof) which is detected by the optimum pressure sensing element 29A as the pulse wave sensor pressing force is increased at a constant low rate, for determining the first force range Pp within which the pulse amplitudes are generally constant and which includes a pressing force at which the optimum pressure sensing element 29A has detected the pulse having the maximum amplitude. In addition, the present apparatus determines the second force range Pd within which the pulse minimum magnitudes are generally constant. In Step S19 of the flow chart of FIG. 3 the overlap portion Pc of the first and second force ranges Pp and Pd is determined as the optimum force range. So long as the pulse wave sensor 20 is pressed with a pressing force falling within the optimum force range, the pulse wave sensor 20 detects a pulse wave having a sufficiently great amplitude. In Step S21 the middle value of the overlap portion Pc is determined as the optimum pulse wave sensor pressing force Pa. Therefore, the optimum pressing force Pa falls between the middle value of the first force range Pp and the middle value of the second force range Pd. Thus, even if the pulse wave sensor pressing force is changed due to physical motion of the subject or the like during the pulse wave detection, the present apparatus continues to detect a pulse wave having a sufficiently great amplitude.

In the present embodiment, in Step S20 it is judged whether or not a difference APc between an upper and a lower limit of the overlap portion Pc is greater than 100 mmHg, and if the judgement in Step S20 is affirmative a value obtained by adding 50 mmHg to the lower limit Pcmin is used as the optimum pressing force Pa. This optimum pressing force Pa is smaller than the middle value of the overlap portion Pc. Thus, in the event that the overlap portion Pc is considerably wide, the present apparatus determines the optimum pressing force Pa at a relatively low value and thereby reduces discomfort of the subject due to the pressed pulse wave sensor 20.

Although in the graph of FIG. 4 the second force range Pd overlaps an upper portion of the first force range Pp, the second force range Pd may overlap a lower portion of the first force range Pd. In the latter case, the optimum pressing force Pa is determined at a value smaller than a pressing force at which the optimum pressure sensing element 29A has detected the maximum pulse amplitude. Thus, the present apparatus uses the optimum pressing force Pa smaller than an optimum pressing force that has conventionally been used by the known apparatus in which a pressing force at the time of detection of the maximum pulse amplitude is used as the optimum pressing force.

In the present embodiment, in Step S18 it is judged whether the second force range Pd is not zero. This is why there are some cases where the second force range Pd is zero, namely, the minimum values of the pulses detected by the optimum pressure sensing element 29A have no range within which differences between the pulse minimum magnitudes are smaller than a predetermined considerably small value. In those cases the first force range Pp is determined as the optimum force range, and the optimum pressing force Pa is determined based on the first force range Pp only. Thus, in the event that the first force range Pp is not zero, the apparatus does not fail to detect a pulse wave, even if the second force range Pd is zero.

In addition, in the present embodiment, in Step S14 it is judged whether the first force range Pp is not zero, and if the judgement is negative (NO), namely, if the first force range Pp is zero, in Step S15 the indication informing that the position of pressing of the pulse wave sensor 20 with respect to the radial artery 30 is inappropriate, is displayed on the display/record device 34, and in Step S16 the ON/OFF switch (not shown) is placed in the OFF position to deactivate the apparatus. Thus, the apparatus easily judges whether or not the pulse wave sensor 20 is appropriately positioned on the body surface 12 with respect to the radial artery 30. In other words, the present apparatus prevents the pulse wave sensor 20 from being located on the body surface 12 at an inappropriate position where the amplitude of pulse wave detected by the pulse wave sensor 20 is relatively largely changed due to a relatively small change in the pulse wave sensor pressing force.

Since in the present embodiment the pulses detected by the pulse wave sensor 20 (pressure sensing elements 29) are subjected to the median filter treatment, the first and second force ranges Pp and Pd are determined with high precision, and accordingly the optimum pressing force Pa is determined in a reliable manner.

While the present invention has been described in its presently preferred embodiment, it is to be understood that the present invention is by no means limited to the particular details of the embodiment but may be otherwise embodied.

For example, in the event that it is judged in Step S20 of the flow chart of FIG. 3 that the value ΔPc is greater than 100 mmHg, it is possible to judge in an additional step whether or not the value ΔPc is greater than another predetermined value greater than 100 mmHg and determine the optimum pressing force Pa in each of the respective ways corresponding to the affirmative and negative judgements in the additional step. Alternatively, Steps S20 and S22 may be omitted, namely, the middle value of the overlap portion Pc may be determined as the optimum pressing force Pa irrespective of the value ΔPc.

Although, in the illustrated embodiment, in Step S22 or S25 the optimum pressing force Pa is determined by adding 50 mmHg, one second of 100 mmHg, to the minimum value Pcmin or Ppmin of the overlap portion Pc or first force range Pp, respectively, it is possible to add a value greater or smaller than 50 mmHg to the minimum value Pcmin or Ppmin.

Furthermore, in the event that the second force range Pd is zero, it is possible to effect additional steps similar to Steps S15 and S16 provided for the event that the first force range Pp is zero.

Although in the illustrated embodiment the optimum pressing force Pa is determined based on the pulse wave signals SM which are produced as the air pressure P in the pressure chamber 22 is increased, it is possible to use pulse wave signals SM which are produced as the air pressure P is decreased, for the determination of the optimum pressing force Pa.

The multiplicity of pressure sensing elements 29 may be replaced by a single pressure sensing element. In addition, the individual pressure sensing elements 29 may be constituted by various elements different from the diodes or other pressure sensing semiconductor elements.

While in the illustrated embodiment the pulse wave sensor 20 is adapted to be pressed against the radial artery 30, it is possible to use a pulse wave sensor adapted to be pressed against an arterial vessel different from the radial artery 30, such as dorsal pedal artery.

It is to be understood that the present invention may be modified with other changes, improvements and modifications that may occur to those skilled in the art without departing from the spirit and scope of the present invention defined in the appended claims.

What is claimed is:

1. A pulse wave detecting apparatus for detecting a pressure pulse wave produced from an arterial vessel of a subject, comprising:

a pulse wave sensor having a press surface on which at least one pressure sensing element is provided, said pulse wave sensor being pressed against an arterial vessel of a subject via a body surface above said arterial vessel so that said at least one pressure sensing element detects a pressure pulse wave produced from said arterial vessel of said subject, said at least one pressure sensing element providing an electric signal representing the detected pressure pulse wave;

pressing means for pressing said pulse wave sensor against said arterial vessel via said body surface, while varying the pressing force thereof over a predetermined force range;

first means for determining an amplitude of each of pulses of the pressure pulse wave represented by said electric signal which is provided by said at least one pressure sensing element while the pressing force of said pressing means is varied;

second means for determining, based on the pulse amplitudes determined by said first means, a first force range of said pressing force within which said pulse amplitudes are generally constant, said first force range including a point at which a rate of change of said pulse amplitudes with respect to said pressing force is zero;

third means for determining a minimum magnitude of said each pulse of the pressure pulse wave represented by said electric signal provided by said at least one pressure sensing element;

fourth means for determining, based on the pulse minimum magnitudes determined by said third means, a second force range of said pressing force within which said pulse minimum magnitudes are generally constant, said second force range including a point at which a rate of change of said pulse minimum magnitudes with respect to said pressing force is minimum;

fifth means for determining, as an optimum force range of said pressing force, at least a portion of said first and second force ranges, and determining an optimum value of said pressing force such that said optimum value falls within said optimum force range; and sixth means for adjusting said pressing means to said optimum value of said pressing force, and obtaining a pressure pulse wave of said subject through said pulse wave sensor pressing against said arterial vessel with the optimum pressing force.

2. The apparatus as set forth in claim 1, wherein, in the event that neither said first force range nor said second force range is zero, said fifth means determines as said optimum force range an overlap portion of said first and second force ranges.

3. The apparatus as set forth in claim 2, wherein, in the event that a value $\Delta Pc$ obtained by subtracting a lower limit Pcmin of said overlap portion from an upper limit thereof is smaller than a first predetermined value S, said fifth means determines said optimum pressing force Pa by the following expression: $Pa = Pcmin + \Delta Pc/2$, and, in the event that said value $\Delta Pc$ is not smaller than said first predetermined value S, said fifth means determines said optimum pressing force Pa by the following expression: $Pa = Pcmin + S/2$.

4. The apparatus as set forth in claim 1, wherein, in the event that said first force range is not zero and said second force range is zero, said fifth means determines said first force range as said optimum force range.

5. The apparatus as set forth in claim 4, wherein, in the event that a value $\Delta Pp$ obtained by subtracting a lower limit Ppmin of said first force range from an upper limit thereof is smaller than a second predetermined value T, said fifth means determines said optimum pressing force Pa according to the following expression: $Pa = Ppmin + \Delta Pp/2$, and, in the event that said value $\Delta Pp$ is not smaller than said second predetermined value T, said fifth means determines said optimum pressing force Pa according to the following expression: $Pa = Ppmin + T/2$.

6. The apparatus as set forth in claim 1, further comprising means for, in the event that said first force range is zero, informing an operator that a position of said pulse wave sensor on said body surface with respect to said arterial vessel is inappropriate, and causing the pulse wave detecting apparatus to be deactivated.

7. The apparatus as set forth in claim 1, wherein said pressing means comprises:

a housing;

a diaphragm fluid-tightly secured to inner surfaces of said housing, said diaphragm cooperating with said housing to define a fluid-tight pressure chamber, said pulse wave sensor being secured to an outer surface of said diaphragm so that said pulse wave sensor is movable together with said diaphragm relative to said housing;

supply means for supplying said pressure chamber with a pressurized fluid so as to press said pulse wave sensor against said arterial vessel via said body surface; and pressure regulating means for regulating said pressurized fluid supplied to s id pressure chamber and thereby adjusting a fluid pressure in said pressure chamber, said pressing force of said pressing means with which said pulse wave sensor is pressed against said arterial vessel being varied as said fluid pressure is varied by said pressure regulating means.

8. The apparatus as set forth in claim 1, wherein said pulse wave sensor comprises:
- a semiconductor chip of monocrystalline silicon; and
- a plurality of pressure sensing diodes provided in a row on one surface of said semiconductor chip, said one surface of said semiconductor chip serving as said press surface of said pulse wave sensor, each of said plurality of pressure sensing diodes detecting a pulse wave produced from said arterial vessel.

9. The apparatus as set forth in claim 1, wherein said at least one pressure sensing element comprise a plurality of pressure sensing elements, and wherein (a) said first means determines an amplitude of each of pulses of the pulse wave which are detected by each of said plurality of pressure sensing elements while said pressing force of said pressing means is varied, (b) said second means selects as an optimum pressure sensing element one of said plurality of pressure sensing elements which element has detected a pulse whose amplitude is the greatest of the amplitudes of the pulses detected by said plurality of pressure sensing elements, and determines said first force range based on the amplitudes of the pulses detected by said optimum pressure sensing element, (c) said third means determines an minimum magnitude of each of the pulses detected by said optimum pressure sensing element, and (d) said fourth means determines said second force range based on the pulse minimum magnitudes determined by said third means.

10. The apparatus as set forth in claim 9, wherein said plurality of pressure sensing elements comprise at least three pressure sensing elements provided in a row on said press surface of said pulse wave sensor, the apparatus further comprising means for, in the event that said second means selects as said optimum pressure sensing element one of two pressure sensing elements respectively positioned at opposite ends of said row, discarding the pressure sensing element selected by said second means, and re-selecting as said optimum pressure sensing element another pressure sensing element which has detected a pulse whose amplitude is the greatest of the amplitudes of the pulses detected by said at least three pressure sensing elements except the discarded pressure sensing element.

11. The apparatus as set forth in claim 1, further comprising means for displaying and recording said pulse wave detected through said pulse wave sensor pressed with said optimum pressing force.

12. The apparatus as set forth in claim 1, further comprising means for determining a blood pressure of said subject based on said pulse wave detected through said pulse wave sensor pressed with said optimum pressing force.

* * * * *